US006584411B1

(12) United States Patent
Geysen (10) Patent No.: US 6,584,411 B1
(45) Date of Patent: Jun. 24, 2003

(54) METHODS TO FACILITATE THE CALCULATION OF YIELDS OF REACTION PRODUCTS

(75) Inventor: H. Mario Geysen, Chapel Hill, NC (US)

(73) Assignee: SmithKline Beecham Corporation, Philadelphia, PA (US)

(*) Notice: Subject to any disclaimer, the term of this patent is extended or adjusted under 35 U.S.C. 154(b) by 110 days.

(21) Appl. No.: 09/625,781

(22) Filed: Jul. 26, 2000

(51) Int. Cl.$^7$ .................................................. G01N 5/00
(52) U.S. Cl. ............................ 702/22; 702/23; 702/26
(58) Field of Search ............................ 364/499, 497; 702/22, 23, 26; 422/22, 68.1

(56) References Cited

U.S. PATENT DOCUMENTS

| 5,463,564 | A |   | 10/1995 | Agrafiotis et al. ........... 364/496 |
| 5,549,974 | A |   | 8/1996  | Holmes ....................... 428/403 |
| 5,574,656 | A |   | 11/1996 | Agrafiotis et al. ........... 364/500 |
| 5,668,373 | A | * | 9/1997  | Robbat, Jr. et al. ...... 250/339.12 |
| 5,684,711 | A |   | 11/1997 | Agrafiotis et al. ........... 364/500 |
| 5,710,713 | A | * | 1/1998  | Wright et al. ............... 364/498 |
| 5,770,358 | A |   | 6/1998  | Dower et al. .................. 435/6 |

FOREIGN PATENT DOCUMENTS

| GB | 2 304 410   | 3/1997  |
| WO | WO 94/08051 | 4/1994  |
| WO | WO 95/28640 | 10/1995 |
| WO | WO 96/30392 | 10/1996 |
| WO | WO 97/08190 | 3/1997  |
| WO | WO 97/14814 | 4/1997  |
| WO | WO 97/37953 | 10/1997 |
| WO | WO 01/97964 | 12/2001 |

OTHER PUBLICATIONS

Geysen, H.M. et al., "Isotope or mass encoding of combinatorial libraries," *Chemistry & Biology*, Aug. 1996, vol. 3, No. 8, pp. 679–688.

Larock, R., "A Guide to Functional Group Preparations," *Comprehensive Organic Transformations*, VCH Publishers, Inc., 1989, pp. xiii–xxviii.

Lutz–Friedjan, T, et al., *Reactions and Syntheses In the Organic Chemistry Laboratory*, University Science Books, 1989, p. 50.

Laidler, K. J., *Chemical Kinetics*, HarperCollinsPublishers, Inc., 1987, p. 22.

(List continued on next page.)

*Primary Examiner*—Marc S. Hoff
*Assistant Examiner*—Felix Suarez
(74) *Attorney, Agent, or Firm*—Frank P. Grassler (57) ABSTRACT

A method for calculating the yield of a reaction product comprises providing a solid support with a first link, a reference material, and a second link having an attachment site. Chemistry is performed on the attachment site of the second link in one or more steps to produce a reaction product. The amount of the reference material and the reaction product is measured, and the percentage yield of the reaction product is determined based at least in part on the amount of measured reference material and the amount of measured reaction product.

15 Claims, 11 Drawing Sheets

OTHER PUBLICATIONS

Willoughby, R. et al., *A Global View of LC/MS How to solve your most challenging analytical problems*, Global View Publishing, 1998, First Edition, pp. 287–293.

Greene, T. W., *Protective Groups in Organic Synthesis*, John Wiley & Sons, Inc., Second Edition, 1991, pp. 1–4; xi–xvi.

Czarnik, "Encoding strategies in combinatorial chemistry," *Proceedings of the National Academy of Sciences of USA* 94:12738–12739 (Nov. 1997).

Fitch et al., "Chemiluminescent Nitrogen Detection for HPLC: An important new tool in organic analytical chemistry," *Tetrahedron Letters* 38(10):1689–1692 (Mar. 1997).

Geysen et al., "Isotope or mass encoding of combinatorial libraries," *Chemistry and Biology, Current Biology* 3(8):679–688 (Aug. 1996).

Ohlmeyer, et al., "Complex synthetic chemical libraries indexed with molecular tags," *Proceedings of the National Academy of Sciences of USA* 90:10922–10926 (Dec. 1993).

* cited by examiner

METHODS TO FACILITATE THE CALCULATION OF YIELDS OF REACTION PRODUCTS

BACKGROUND OF THE INVENTION

The invention relates generally to the field of chemistry, and in particular to the measurement of yields of reaction products. In one specific aspect, the invention relates to the use of mass spectroscopy to assist in determining the yields of reaction products. The invention also relates to techniques that may be used to potentially increase the yields of reactions.

An important pursuit of modern chemistry is the production of a wide variety of chemical products that may be used in numerous applications, such as, for example, pharmaceuticals, cleaners, paints, and the like. To produce such chemicals, one or more chemicals are reacted to produce one or more reaction products.

Many techniques for producing chemical products utilize solid supports having one or more linking sites where chemistries are performed. Further, one or more combinatorial processes may be employed as various chemical building blocks are reacted in a reaction sequence. Such techniques are efficient at producing relatively large chemical libraries. However, with these large libraries, relatively small amounts of each reaction products is produced, making it difficult to efficiently determine the yield of those reaction products. Even so, when producing reaction products, the resulting yield is of immense importance to chemists. Identification of the reaction conditions giving the highest yield of the desired product is both desirable and of commercial significance.

Hence, the invention relates to techniques for measuring the yield of reaction products in an efficient and a high throughput manner. Also, the invention relates to techniques for potentially increasing the yield of reaction products.

SUMMARY OF THE INVENTION

In one aspect of the invention, a method is provided for calculating the yield of a reaction product. The method utilizes a solid support with a first link, a reference material, and a second link having an attachment site. Chemistry is performed on the attachment site of the second link in one or more steps to produce a reaction product. The amount of the reference material and the reaction product are measured, and the percentage yield of the reaction product is determined based at least in part on the amount of measured reference material and the amount of measured reaction product. For example, the measuring step may comprise counting the number of ions of the reference material and the reaction product, and the yield may be determined by dividing the number of counted ions of the reaction product by the number of counted ions of the reference material.

In one aspect, the chemistry performing step comprises reacting the attachment site with a chemical building block to produce the reaction product. Alternatively, the chemistry performing steps may comprise reacting the attachment site with a first chemical building block to produce an intermediate product, and reacting the intermediate product with a second chemical building block to produce the reaction product. In still another alternative, the chemistry performing steps may comprise reacting the attachment site with a first chemical building block to produce an intermediate product, and carrying out a chemical transformation of the intermediate reaction product to produce the reaction product.

In another embodiment, a method for calculating the yields of reaction products using a mass spectrometer comprises counting the number of ions of the reference component and the corresponding reaction products that have been cleaved from multiple solid supports. The efficiency with which the reference materials and the products are detected by a given mass spectrometer is then determined. The percentage yield of each reaction product is calculated based at least in part on the amount of the number of counted ions of the associated reference material, the counted number of ions for the reaction product, and the determined efficiency.

Conveniently, the efficiency with which the mass spectrometer may detect the reference materials and the reaction products may be determined by producing multiple equations where each equation sets the ion counts of each reference material equal to the sum of a coefficient multiplied by the ion counts of the associated reaction product. After solving for the coefficients of the equations, the yields may be calculated by multiplying the coefficients by the number of ion counts of each product and dividing the product by the number of ion counts of the associated reference material.

In yet another embodiment, a method is provided for evaluating the yields of multiple chemical reactions where different reaction conditions are used in an attempt to increase the yield of a given reaction sequence. According to the method, multiple solid supports are provided which each include a first link, a reference material, and a second link having an attachment site. Chemistry is performed on the attachment sites of the second links in one or more steps and under different reaction conditions to produce a reaction product for each solid support. The percentage yield of the reaction products are determined based at least in part the amount of measured reference material. The yields may then be associated with the reaction conditions to determine which reaction conditions provided the best yields. Further, any side products may also be evaluated to determine if the process may be useful in developing a given reaction product.

Conveniently, the solid supports may further include a reaction condition code (which may also serve as the reference material) that is indicative of the reaction conditions used when performing the chemistries. This code may then be decoded to determine the reaction conditions. The use of such a code is particularly useful when the reactions are performed using mix and split techniques as is known in the art. Exemplary reaction conditions which may be employed include time, temperature, solvents, reagents, pressure, catalysts, and the like.

The invention also provides an exemplary chemical construct which comprises a solid support and a linking component having an attachment site. A ligand component is linked to the attachment site. The construct also includes a coding component which includes coded information on at least one reaction condition utilized when producing the ligand component. In this way, the reaction condition may be determined by simply evaluating the coding component. Preferably, the coding component comprises a mass code which is readable using a mass spectrometer. Once the mass of the code is measured, a look-up table is searched to identify the reaction condition.

DESCRIPTION OF THE SPECIFIC EMBODIMENTS

One aspect of the invention relates to the measurement of yields of reaction products. Although useful with essentially any type of reaction product, the invention may find particular use with reaction products created using the techniques of combinatorial chemistry where one or more chemical building blocks are reacted to a linking site on a solid support. For example, the invention may find use with chemical libraries produced using the chemical constructs as described generally in H. Mario Geysen, et al., "Isotope or Mass Encoding of Combinatorial Libraries," Chem. & Biol. Vol. III, No. 8, pp. 679–688, August 1996, and PCT International No. PCT/US97/05701, the complete disclosures of which are herein incorporated by reference. Further, although useful with solid phase chemistry, it will be appreciated that the techniques of the invention may be applied to solution phase chemistry as well. For example, the techniques of the invention may be used with the solution phase constructs described in copending U.S. application Ser. No. 09/625, 782, filed on the same date as the present application, the complete disclosure of which is herein incorporated by reference.

Once the libraries have been created, one convenient way to evaluate the products and their yields is by the use of mass spectroscopy. According to the invention, samples are cleaved from the solid supports and placed in solution. The solution is injected into a mass spectrometer where the fine spray is ionized, passed through one or Once the libraries have been created, one convenient way to evaluate the products and their yields is by the use of mass spectroscopy. According to the invention, samples are cleaved from the solid supports and placed in solution. The solution is injected into a mass spectrometer where the fine spray is ionized, passed through one or more small apertures and into chamber where the ions are separated and counted. The use of mass spectrometers to separate and count ions is well known within the art and will not be described further. Alternatively, other techniques that are known in the art may be used to measure the resulting materials, including spectrophotometric methods.

When using a mass spectrometer to evaluate the reaction products, different molecules may be processed differently by the mass spectrometer. As such, the number of counted ions for each molecule may not be in the same proportion as is found in the injected solution containing the reaction products. Factors that may have an effect on the way that the molecules are processed and counted include, for example, the degree of ionization, the manner in which the molecular species are transferred from droplet form to the gas phase, the efficiency with which the molecular species are transferred to the low pressure side of the mass spectrometer, and the like.

The invention compensates for such effects by utilizing a reference material that is linked to the solid support. A second link is coupled to the reference material and has a linking site where chemistries are performed. With such a configuration, multiple samples may be cleaved from the solid supports and placed into a mass spectrometer to count the ions of the reference material and any starting materials, intermediate products or end reaction products. Multiple equations may be produced that include one or more coefficients that are a function of the efficiency with which the materials and products may be detected by the mass spectrometer. Given enough a equations, the coefficients may be determined. Optionally, numerous additional equations may be used and a statistical analysis performed on the resulting coefficients to further define each of the coefficients.

The yields may then be determined by multiplying the ion counts of the reaction product by its associated coefficient and dividing the product by the ion counts of the reference material. Alternatively, yield values may be obtained by producing standard curves for each of the reaction products and using the curve to look up an associated yield.

Use of the mass spectrometer is advantageous in that large numbers of samples may be evaluated in a relatively short time. An example of a mass spectrometer that may be used is an API 100, LC/MS system spectrometer, commercially available from Perkin-Elmer Sciex Instruments, Foster City, Calif. The mass spectrometer produces a mass spectra having a variety of peaks which represent the reference material, any starting materials, intermediate products and end reaction products. The mass spectrometer identifies the molecular weight associated with each peak, the peak width and the peak area. Software code may also be provided to search for signatures associated with the peaks of interest. For example, as described hereinafter, such software code may search for adjacent peaks which are spaced-apart by one AMU and have the same area. Such a technique is described generally in H. Mario Geysen, et al., "Isotope or Mass Encoding of Combinatorial Libraries," Chem. & Biol. Vol. III, No. 8, pp. 679–688, August 1996, and PCT International No. PCT/US97/05701, previously incorporated by reference. From this information, product yield values may be determined as just described. Some or all of this information may be stored in a searchable database. Hence, by utilizing a mass spectrometer, a relatively simple and economical way is provided to populate the database. This information may then be searched or used to perform simulated reactions. Other ways to measure reaction products and associated yields include, but are not limited to, ultraviolet quantitation, gravimetric quantitation, quantitation based on fluorescent, nitrogen and NMR, and the like.

The invention may utilize chemical constructs which are covalently bonded entities comprising, in any combination, some type of solid support, one or more linking components, one or more ligands, and optionally, one or more ligand coding components and/or reaction condition coding components. Further, a mass based reference block or material may also be used when determining yields as previously described. Conveniently, any ligand coding or reaction conditioning components as described in greater detail hereinafter may also be used as the reference block.

Figure 1:
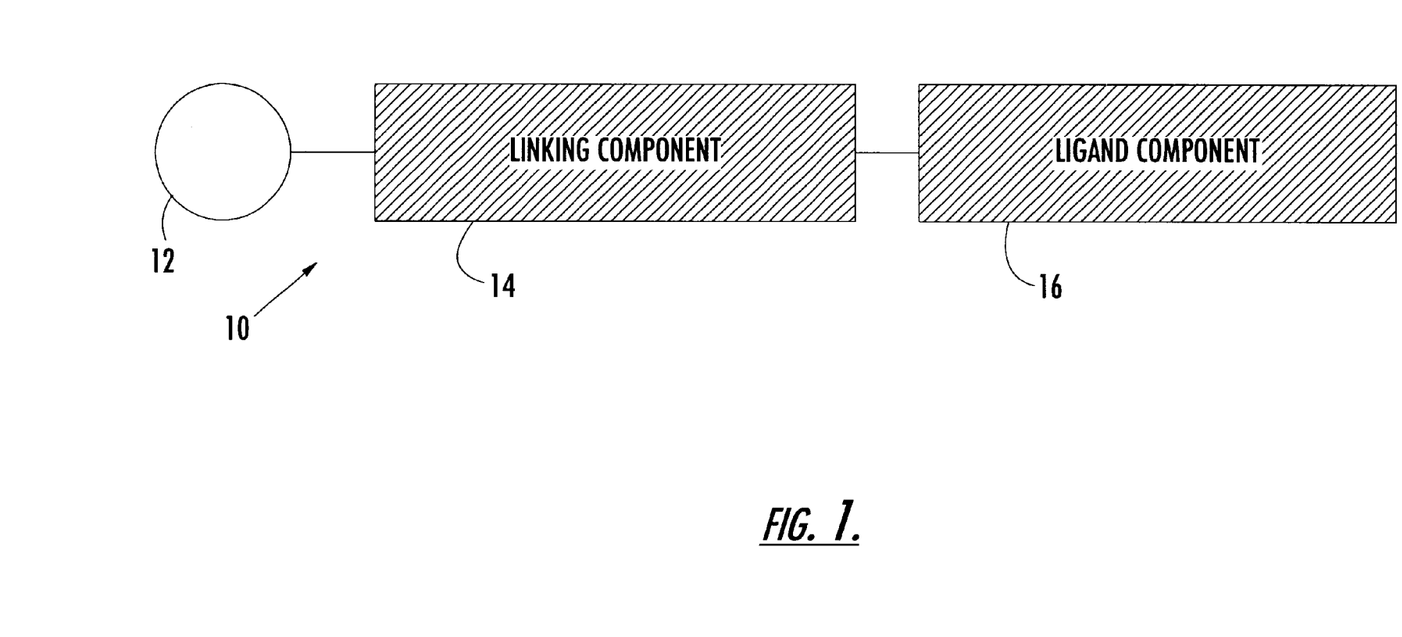
FIG. 1 is a schematic diagram of an exemplary chemical construct according to the invention.

One embodiment of a chemical construct 10 is illustrated in FIG. 1 and comprises a solid support 12, a linking component 14, and a ligand component 16. The solid supports used by the invention may be constructed of one or more materials upon which combinatorial chemistry synthesis can be performed, including beads, solid surfaces, solid substrates, particles, pellets, discs, capillaries, hollow fibers, needles, solid fibers, cellulose beads, pore glass beads, silica gel, polystyrene beads, optionally cross-linked with divinylbenzene, grafted copoly beads, polyacrylamide beads, latex beads, dimethylacrylamide beads, optionally cross-inked with N, N'-bis-acryloyl ethylene diamine, glass particles coated with a hydrophobic polymer, fullerenes and soluble supports, such as low molecular weight, nuncios-linked polystyrene. The linking component may be any covalent bond or molecular moiety that is suitable for linking two portions of a construct together.

The ligands of the invention may comprise any chemical reaction product of interest. For example, a ligand may be part of a larger construct, where the ultimate goal will be to identify and/or cleave the ligand part from the rest of the construct. The ligand coding components of the invention are preferably components which may be linked to a solid support and which contain information about at least one of the chemicals used to construct a ligand which is also linked to the solid support. As previously mentioned, the ligand code may also serve as a reference material when determining the yield of a reaction. The reaction condition coding components are components which may be linked to a solid support and which contain information about one or more reaction conditions existing when the ligand is constructed. Such reaction conditions can include, for example, time, temperature, solvents, reagents, catalysts, pressure, and the like as previously described. Other reaction conditions which may be employed by the invention include those described in Lutd-Friadjan Tietze, Reaction and Synthesis in the Organic Chemistry Library, University Science Books (1989) and Richard C. Larock, Comprehensive Organic Transformation—A Guide to Functional Group Preparation, VCH Publishers, Inc., (1989), the complete disclosures of which are herein incorporated by reference.

Figure 2:
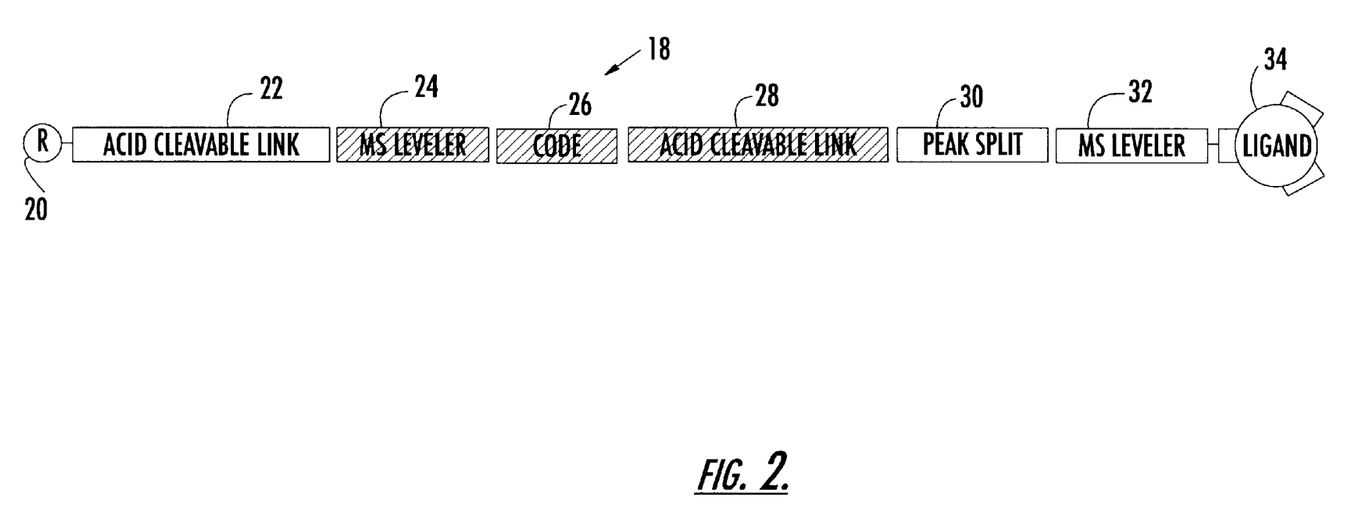
FIG. 2 is a schematic diagram of a another chemical construct according to the invention.

As previously mentioned, the information contained within the constructs may be evaluated using a mass spectrometer. Use of mass spectrometry is advantageous in that modern computers may then be employed to assist in the analysis of mass spectra of large numbers of independent reactions. One exemplary construct that may be employed by the invention and which is also useful with mass spectrometry analysis is illustrated in FIG. 2. Construct 18 comprises a resin solid support 20 to which is coupled an acid cleavable link 22, mass spectrometry (MS) leveler 24, a ligand code 26, an acid cleavable link 28, a peak splitter 30, a MS leveler 32, and a ligand 34 as described generally in PCT International No. PCT/US97/05701. Links 22 and 28 allow code 26 and ligand 34 to be cleaved from solid support 20. In this way, all of the resin bound particles of a solid phase reaction process may be identified. Further, as described in greater detail hereinafter, the yields of all reaction products may be identified.

Code 26 is preferably employed to identify one or more building blocks from which ligand 34 was constructed during synthesis. Typically, ligand code 26 will be employed when construct 18 is produced using a mix and split method, such as one of the methods described in H. Mario Geysen, et al., "Isotope or Mass Encoding of Combinatorial Libraries," Chem. & Biol. Vol. III, No. 8, pp. 679–688, August 1996; PCT International No. PCT/US97/05701; and copending U.S. application Ser. No. 09/289, 211, filed Apr. 9, 1999, the complete disclosures of which are herein incorporated by reference. Although not shown, a reaction condition coding component may also be included as described in greater detail hereinafter.

MS levelers 24 and 32 are readily ionizable basic functionalities, such as a primary amino acid group, that are employed to ionize ligand code 26 and ligand 34 to make them useful with a mass spectrometer to allow reaction products and unreacted molecules to be readily identified. Peak splitter 30 is employed to provide a unique and easily recognized mass profile on the output of the mass spectrometer. Such peak splitting may be obtained, for example, by introducing into link 28 a predefined mixture of two chemically identical components differing in absolute mass. Alternatively, peak splitting may be obtained by using an appropriate mixture of two versions of link 28, differing in isotopic composition of the atom transferred at the cleavage step as described generally in H. Mario Geysen, et al., "Isotope or Mass Encoding of Combinatorial Libraries," Chem. & Biol. Vol. III, No. 8, pp. 679–688, August 1996, and PCT International No. PCT/US97/05701, previously incorporated by reference. With either method, peak splitting by one or more atomic mass units (AMU) is readily obtained.

Figures 3, 3A, 3B, 3C, 3D:
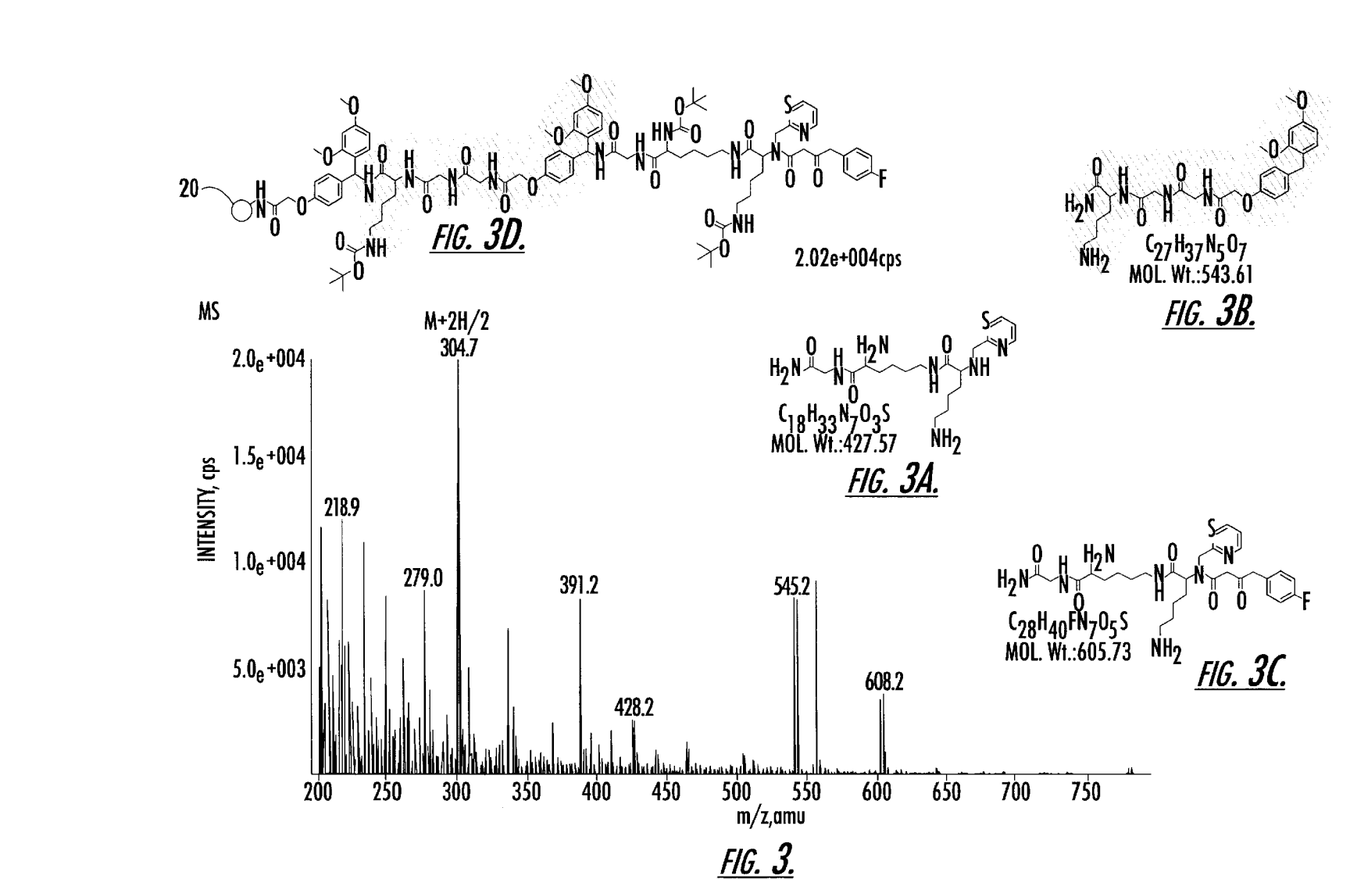
FIG. 3 illustrates a graph produced by a mass spectrometer when analyzing information from a chemical construct, such as the construct of FIG. 2, according to the invention.
FIGS. 3A–3C illustrate three reaction products identified in the graph of FIG. 5.

As one example, FIG. 3 illustrates the resulting mass spectrum of various products observed after cleavage of ligand 34 at link 28 (see FIG. 2). FIGS. 3A–3C illustrate the three reaction products of ligand 34, while FIG. 3D illustrates the molecular structure of the entire construct 18. As shown in FIG. 3, the peaks at 428.2 AMU 545.2 AMU, and 608.2 AMU each have a split. In this way, the resulting products may easily be identified by simply evaluating locations on FIG. 3 where a peak had split. Ligand code 26 is identified by evaluating a predetermined region in the mass spectra. The predetermined region is selected so that it will always include the mass of code 26. Within this region, a search is performed to identify the peak corresponding to code 26. A look-up table is then employed to decode the code and determine the functional groups employed in the reaction as described in PCT International No. PCT/US97/05701.

To identify the peak splits produced by the mass spectrometer, the mass spectrometer (or another computer coupled to the mass spectrometer) is preferably provided with software which compares peaks to determine if they have approximately the same intensity. An exemplary mass spectrometer which may be programmed to function in such a manner is an API 100, LS/MS System mass spectrometer, commercially available from Perkin-Elmer Sciex Instrument.

Figures 4A, 4B:
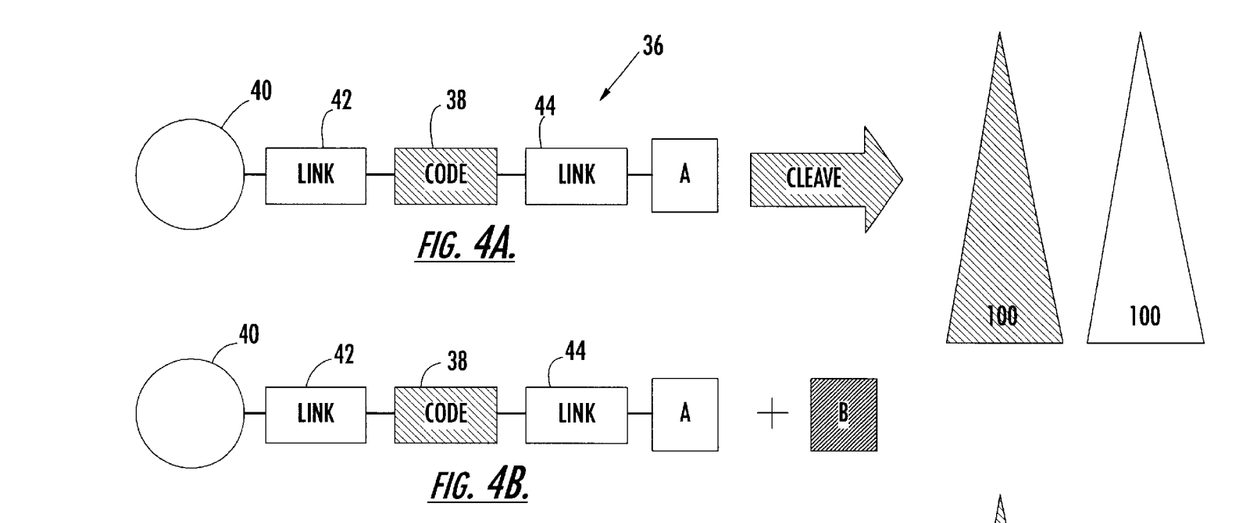
FIGS. 4A–4C schematically illustrate an exemplary process for quantifying the amount of chemicals involved in a chemical reaction according to the invention.

As previously mentioned, the invention provides techniques for determining quantity or yield information for each of the reaction products. Hence, in addition to identifying each reaction product using a mass spectrometer, the invention also employs the mass spectrometer to identify the relative quantity or yield of each reaction product. A schematic illustration of such a process is set forth in FIGS. 4A–4C. In FIG. 4A, a construct 36 is shown with a building block A that is attached to a linking site of link 44. A reference block 38 is linked to a solid support 40. Block 38 is used as a reference component when determining the percentage yield of each reaction product as described in greater detail hereinafter. Conveniently, block 38 may also serve as a ligand code as previously described in connection with constructs 10 and 18. As described hereinafter, block 38 may also serve as a reaction condition code. After building block A has been synthesized onto solid support 40, links 42 and 44 are cleaved and block 38 and building block A are evaluated using a mass spectrometer to produce a graph of molecular weight versus intensity. The resulting graph includes a curve having peaks disposed above the molecular weight value for the ions associated with block 38 and building block A. As shown in FIG. 4A, the area under both of these peaks, i.e. the number of ion counts, is mathematically scaled to be 100 units. The other peaks in the spectrum may conveniently be scaled by the same amount.

Figure 4C:
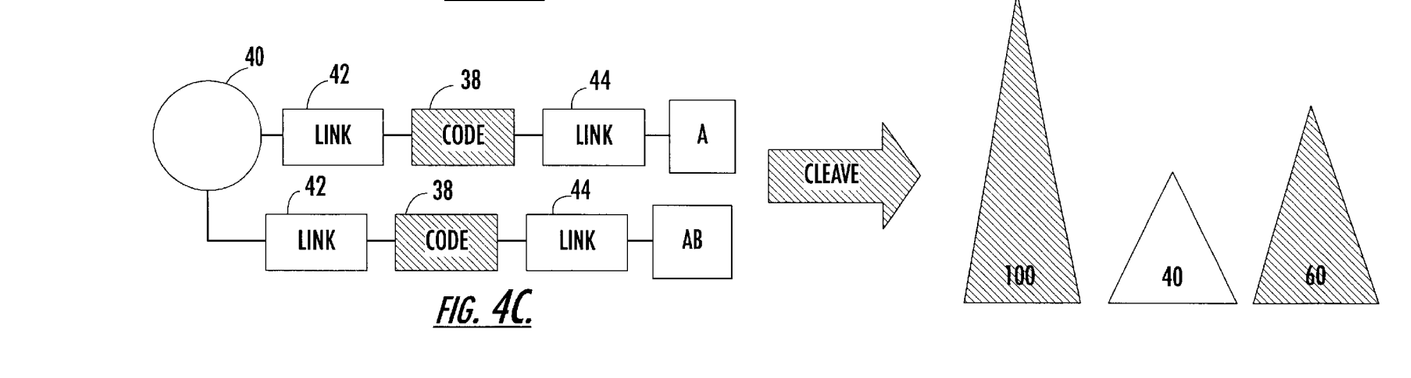

The process then proceeds to FIG. 4B where a building block B is reacted with building block A. As shown in FIG. 4C, this produces a reaction product AB. Reference block 38, building block A and reaction product AB are then cleaved and evaluated under mass spectrometry. As shown in FIG. 4C, the area of block 38, i.e. the number of ion counts, remains at 100 units, while the area of building block A is 40 units. The area under reaction product AB is 60 units. From this information, it may be determined that reacting building block A with building block B under a given set of reaction conditions produces a 60% yield. Use of such a method is made possible because chemical reactions are described with a stoichiometry for each reactant and product to preserve the total number of each type of atom involved.

Although the foregoing example utilized two building blocks A and B, it will be appreciated that other chemistries may also be employed. For example, after reacting building block A with the linking site, a reagent may be used to transform building block A into a product A'. As another example, a three (or greater) reaction sequence may be employed to react three or more building blocks.

Figure 5:
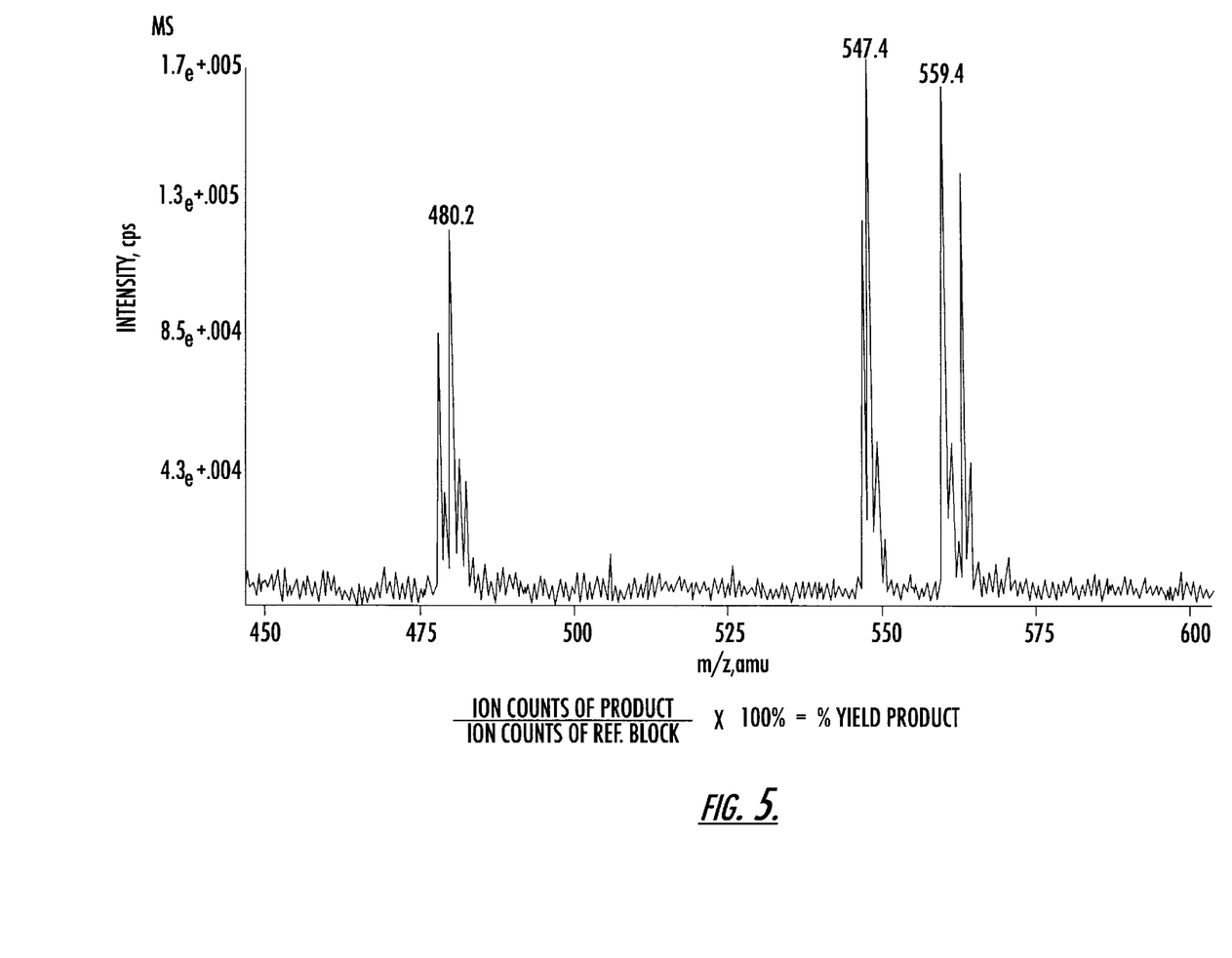
FIG. 5 illustrates one specific example of calculating the yield of a reaction product relative to a reference block when utilizing a graph produced by a mass spectrometer according to the invention.
Figure 5A:
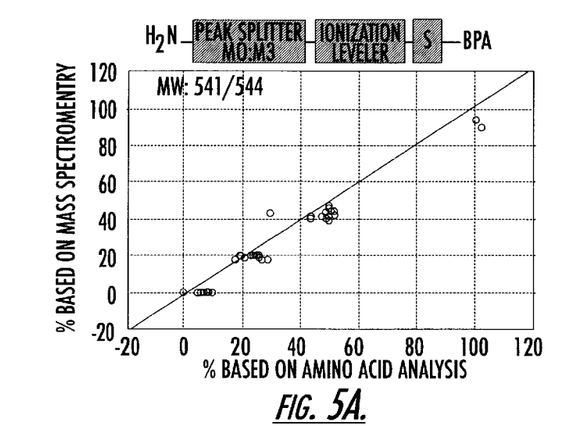
FIGS. 5A–5D are graphs illustrating the correlation between a mass spectrometer analysis of a selected synthesis with an amino acid analysis.
Figure 5B:
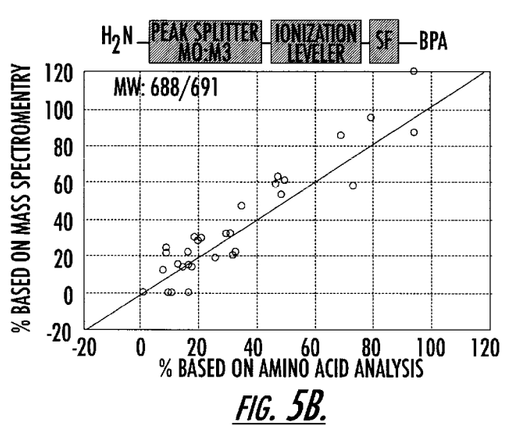
Figure 5C:
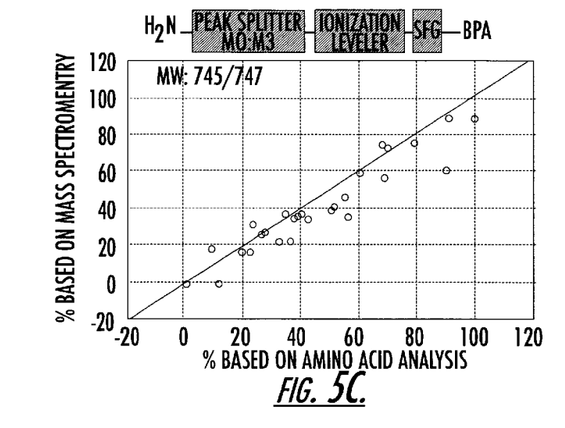
Figure 5D:
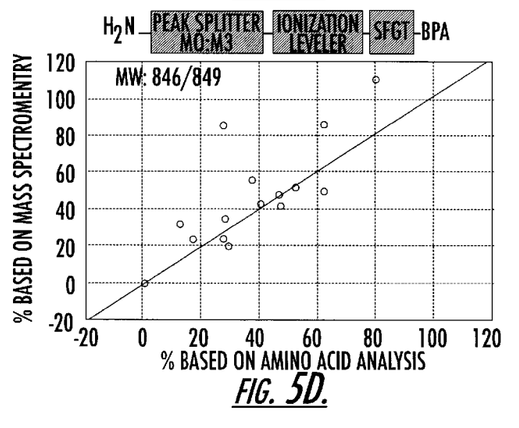

Referring now to FIG. 5, a portion of one exemplary mass spectrum containing a reaction product and a reference block is illustrated. To determine the percent yield with which reaction product was produced, the number of ion counts of the product is divided by the number of ion counts of the reference block and multiplied by 00%. Hence, by using mass spectrometry, computer software may be employed to count the ions for each material or product and then perform a simple comparison to determine yield data for essentially any reaction.

When utilizing mass spectrometry to determine the percentage yield of a given reaction product, it is desirable to compensate for various effects within the spectrometer. Such effects can include, for example, the degree of ionization, the manner in which the molecular species are transferred from droplet form to the gas phase, the efficiency with which the molecular species are transferred to the low pressure side of the mass spectrometer, and the like. One way to compensate for such effects is by producing standard curves for each material. Another convenient way to compensate for such effects is to take advantage of cases where varying amounts of individual products are observed for individual beads (while also normalizing for differences in the bead loading). As previously described, chemical reactions are described with a stoichiometry for each reactant and product to preserve the total number of each type of atom involved. In other words, the number of ion counts obtained from the mass spectrometer for all components directly linked to the solid support, corrected for the effects of the mass spectrometer and bead-loading, is constant.

For example, 100 ion counts of starting material may be seen to reduce to 50 ion counts, and the only product produced is 25 ion counts. By taking advantage of this situation, and by engineering the reference block so that it includes the same number of molecules as the starting material, the effects resulting from the mass spectrometer may be determined by producing simultaneous equations which include certain coefficients. By providing a sufficient number of simultaneous equations, the coefficients may be determined and subsequently used when calculating the yields.

For example, when utilizing the construct of FIG. 4, a set of equations may be defined for each construct as follows: the number of ion counts of the reference block equals $C_0 \times$ the number of ion counts of the starting material $+ C_1 \times$ the number of ion counts of the product $1 + \ldots + C_N \times$ the number of ion counts for the product N. By providing a sufficient number of data points with varying ratios of the possible products, a multivariant linear analysis provides all of the coefficients. Utilizing these coefficients, the absolute yield for all of the components may be determined.

Merely by way of example, three constructs may be provided that include a reference material and a building block A. With one of the constructs, building block A is reacted with building block B to produce the product of A+B. With another one of the constructs, the product of A+B is then reacted with C to produce the product of A+B+C. Assuming that C does not react with A, three simultaneous equations may produced for the three constructs by evaluating A before a combination with B, by evaluating the product of A+B before combination with C, and by evaluating the product of A+B+C. This provides the following set of equations:

$$I_{reference\ material\ 1} = C_A I_A$$

$$I_{reference\ material\ 2} = C_A I_A + C_{AB} I_{AB}$$

$$I_{reference\ material\ 3} = C_A I_A + C_{AB} I_{AB} 30\ C_{ABC} I_{ABC}$$

Where I=the number of ion counts. With three unknowns and three equations, the coefficients may be determined. The yield of the reaction products may then be determined using the coefficients.

In some cases, it may be desirable to provide additional equations and then perform a statistical analysis on the coefficients. For example, another equation that may be used is:

$$I_{reference\ material\ 4} = C_A I_A + C_{AB} I_{AB} + C_{ABC} I_{ABC}\ (\text{reaction time 2}).$$

EXAMPLE

The following example is one non-limiting example that illustrates the above described technique. In this example, 192 beads were picked from a mix and split library synthesis. Spectra was collected from a mass spectrometer for each bead through the various steps of synthesis to produce 192 equations as set forth below:

| Bead # | Area Ref. | Area P1 | Area P2 | Area P3 | Area P4 |
|---|---|---|---|---|---|
| 1 | 387.1 | 325.7 | 0 | 0 | 0 |
| 2 | 318 | 131.2 | 180.7 | 0 | 0 |
| 3 | 404 | 76.6 | 339.5 | 0 | 0 |
| 4 | 576.2 | 0 | 677.4 | 0 | 0 |
| 5 | 632.9 | 266.6 | 375.2 | 0 | 0 |
| 6 | 496.1 | 198.5 | 144.5 | 97.6 | 0 |
| 7 | 583 | 233.2 | 65.9 | 171.7 | 0 |

| Bead # | Area Ref. | Area P1 | Area P2 | Area P3 | Area P4 |
|---|---|---|---|---|---|
| 8 | 641.1 | 251.5 | 0 | 256.6 | 0 |
| 9 | 696.5 | 118.2 | 573.6 | 0 | 0 |
| 10 | 615.1 | 117 | 283.8 | 188 | 0 |
| 11 | 541.6 | 102.6 | 111.1 | 259.9 | 0 |
| 12 | 751.9 | 144.8 | 0 | 482.1 | 0 |
| 13 | 643 | 0 | 601.5 | 0 | 0 |
| 14 | 682.5 | 0 | 349.6 | 217.2 | 0 |
| 15 | 473.8 | 0 | 109.5 | 244.3 | 0 |
| 16 | 483.6 | 0 | 0 | 362.7 | 0 |
| 17 | 556.6 | 231.2 | 75.2 | 172.2 | 0 |
| 18 | 496.1 | 220.8 | 74.7 | 118.1 | 54.7 |
| 19 | 474.7 | 185.7 | 57.2 | 50.4 | 69.7 |
| 20 | 472.1 | 208 | 68.2 | 0 | 136.7 |
| 21 | 566.9 | 216.1 | 0 | 203.4 | 0 |
| 22 | 532.4 | 217.8 | 0 | 144 | 44.2 |
| 23 | 583.7 | 241.8 | 0 | 83.2 | 70.3 |
| 24 | 650.9 | 259.8 | 0 | 0 | 95.8 |
| 25 | 715.6 | 137.8 | 152.8 | 361.2 | 0 |
| 26 | 686.5 | 126.9 | 135.1 | 187.8 | 57.3 |
| 27 | 684.6 | 133 | 148.6 | 109.1 | 129.4 |
| 28 | 577.2 | 104.3 | 106.9 | 0 | 102.2 |
| 29 | 736 | 125.7 | 0 | 451 | 0 |
| 30 | 731.4 | 126.8 | 0 | 224.9 | 49.7 |
| 31 | 450.7 | 87.2 | 0 | 86.4 | 72.8 |
| 32 | 692.8 | 125.6 | 0 | 0 | 203.6 |
| 33 | 566.5 | 0 | 159.7 | 358.6 | 0 |
| 34 | 637.2 | 0 | 176.4 | 214.7 | 52.9 |
| 35 | 746.2 | 0 | 234.7 | 108 | 107 |
| 36 | 689.5 | 0 | 136.1 | 0 | 117.1 |
| 37 | 562.3 | 0 | 0 | 423 | 0 |
| 38 | 669.6 | 0 | 0 | 244.2 | 108.2 |
| 39 | 831.8 | 0 | 0 | 138.8 | 231.6 |
| 40 | 675.9 | 0 | 0 | 0 | 252.8 |
| 41 | 548.7 | 485.8 | 0 | 0 | 0 |
| 42 | 746.8 | 312.5 | 457.9 | 0 | 0 |
| 43 | 720.9 | 140.3 | 665.2 | 0 | 0 |
| 44 | 947.6 | 0 | 803.7 | 0 | 0 |
| 45 | 601.3 | 222.6 | 346.1 | 0 | 0 |
| 46 | 514.5 | 200.2 | 160.3 | 115.3 | 0 |
| 47 | 547.8 | 209.4 | 72.8 | 174.6 | 0 |
| 48 | 823.6 | 321.9 | 0 | 352.5 | 0 |
| 49 | 708.6 | 136.9 | 604.9 | 0 | 0 |
| 50 | 839.9 | 159.1 | 387.7 | 250 | 0 |
| 51 | 515.2 | 108.1 | 118 | 271.2 | 0 |
| 52 | 897.5 | 164.1 | 24.7 | 584.3 | 0 |
| 53 | 862.1 | 0 | 973.9 | 0 | 0 |
| 54 | 839.4 | 0 | 563 | 342.3 | 0 |
| 55 | 812.7 | 0 | 234.8 | 545.4 | 0 |
| 56 | 618.8 | 0 | 0 | 513.8 | 0 |
| 57 | 511.6 | 180 | 65.1 | 149.8 | 0 |
| 58 | 501.6 | 197.8 | 71.1 | 110 | 0 |
| 59 | 497.4 | 194.8 | 66.1 | 57.4 | 44.3 |
| 60 | 743.8 | 281.2 | 98.3999 | 0 | 89.6 |
| 61 | 443 | 172.1 | 0 | 176.8 | 0 |
| 62 | 787.5 | 326.2 | 22.4 | 202.4 | 41.3 |
| 63 | 537.5 | 211.5 | 0 | 65.5 | 51.7 |
| 64 | 838 | 369.3 | 0 | 0 | 126.9 |
| 65 | 721.5 | 142.5 | 166.6 | 393 | 0 |
| 66 | 624.4 | 108.4 | 129.4 | 177.8 | 41 |
| 67 | 901.2 | 149.8 | 199.3 | 129.8 | 111.9 |
| 68 | 754.7 | 124.1 | 173.3 | 0 | 121.6 |
| 69 | 780.8 | 128.6 | 29.3 | 422.7 | 0 |
| 70 | 566.2 | 102.5 | 0 | 197 | 60 |
| 71 | 426.6 | 75.8 | 0 | 79.5 | 78.6 |
| 72 | 467 | 78.2 | 0 | 0 | 75.6 |
| 73 | 827 | 0 | 322.3 | 431 | 0 |
| 74 | 754.1 | 0 | 247.3 | 226.5 | 60.5 |
| 75 | 650.3 | 0 | 192.4 | 110 | 113 |
| 76 | 605.7 | 0 | 165.4 | 0 | 132.9 |
| 77 | 847.2 | 0 | 0 | 718 | 0 |
| 78 | 919.7 | 0 | 0 | 391.4 | 174.3 |
| 79 | 970.1 | 0 | 0 | 172 | 271.1 |
| 80 | 550 | 0 | 0 | 0 | 159.3 |
| 81 | 680.4 | 609.7 | 0 | 0 | 0 |
| 82 | 600.1 | 498.9 | 0 | 0 | 0 |
| 83 | 541.4 | 474.8 | 0 | 0 | 0 |
| 84 | 480.3 | 360.6 | 0 | 0 | 0 |
| 85 | 719.2 | 0 | 614 | 0 | 0 |
| 86 | 878.8 | 0 | 722.6 | 0 | 0 |
| 87 | 919.8 | 0 | 1073 | 0 | 0 |
| 88 | 896.8 | 0 | 783.7 | 0 | 0 |
| 89 | 627.4 | 0 | 0 | 525.6 | 0 |
| 90 | 527.1 | 0 | 0 | 366.8 | 0 |
| 91 | 538.6 | 0 | 0 | 446.8 | 0 |
| 92 | 794.9 | 0 | 0 | 640.7 | 0 |
| 93 | 855 | 0 | 0 | 0 | 302.9 |
| 94 | 488 | 0 | 0 | 0 | 127.6 |
| 95 | 589.5 | 0 | 0 | 0 | 169.8 |
| 96 | 436 | 0 | 0 | 0 | 108.8 |
| 97 | 504.9 | 474 | 0 | 0 | 0 |
| 98 | 550.8 | 238.9 | 349 | 0 | 0 |
| 99 | 608.4 | 122.5 | 559.5 | 0 | 0 |
| 100 | 852 | 0 | 753 | 0 | 0 |
| 101 | 754.6 | 324.6 | 443.7 | 0 | 0 |
| 102 | 761.2 | 327.4 | 233.6 | 157.9 | 0 |
| 103 | 485.4 | 204.1 | 61.6 | 129.7 | 0 |
| 104 | 537.3 | 218.3 | 0 | 212.2 | 0 |
| 105 | 944.6 | 151.2 | 755.1 | 0 | 0 |
| 106 | 696.4 | 126.8 | 301.3 | 200.5 | 0 |
| 107 | 524.9 | 103.5 | 112.4 | 257.4 | 0 |
| 108 | 678.2 | 136.1 | 0 | 495.8 | 0 |
| 109 | 949.9 | 0 | 873.6 | 0 | 0 |
| 110 | 741.5 | 0 | 454.3 | 290.6 | 0 |
| 111 | 776.3 | 0 | 194.8 | 461.2 | 0 |
| 112 | 922.8 | 0 | 0 | 834 | 0 |
| 113 | 838.1 | 326.3 | 107.3 | 250.3 | 0 |
| 114 | 1007.2 | 426.7 | 143.5 | 237.5 | 112.9 |
| 115 | 997.8 | 448.7 | 148.7 | 131.2 | 216.9 |
| 116 | 696.1 | 269.6 | 82.6 | 0 | 168.8 |
| 117 | 862.7 | 395.1 | 0 | 419.5 | 0 |
| 118 | 734.7 | 323.8 | 0 | 207.5 | 69.1 |
| 119 | 921.2 | 387.4 | 0 | 125.7 | 110.4 |
| 120 | 973.2 | 443.6 | 0 | 0 | 170.7 |
| 121 | 854.6 | 163.1 | 193.2 | 481.3 | 0 |
| 122 | 1013.8 | 192.3 | 220.4 | 317.3 | 111.1 |
| 123 | 804.9 | 149.3 | 173.9 | 129.9 | 163.3 |
| 124 | 785.8 | 140.2 | 149.5 | 0 | 147.9 |
| 125 | 759.7 | 143.6 | 0 | 521.4 | 0 |
| 126 | 1023.2 | 206.5 | 0 | 424.3 | 102.9 |
| 127 | 869.5 | 177.9 | 0 | 176.9 | 173.7 |
| 128 | 791.4 | 149.7 | 0 | 0 | 265.4 |
| 129 | 795.5 | 0 | 237 | 523.2 | 0 |
| 130 | 629.4 | 0 | 170.1 | 212.8 | 47.8 |
| 131 | 736.7 | 0 | 234.3 | 109.9 | 117.6 |
| 132 | 835.9 | 0 | 174.3 | 0 | 112.7 |
| 133 | 562.6 | 0 | 28.9 | 407.1 | 0 |
| 134 | 704.3 | 0 | 0 | 248 | 110.9 |
| 135 | 833.6 | 0 | 0 | 138.8 | 241 |
| 136 | 874.6 | 0 | 0 | 0 | 322.5 |
| 137 | 735.6 | 687.3 | 0 | 0 | 0 |
| 138 | 666.1 | 294.7 | 428.1 | 0 | 0 |
| 139 | 1109.3 | 175.3 | 838.1 | 0 | 0 |
| 140 | 866.8 | 0 | 727.7 | 0 | 0 |
| 141 | 632.9 | 277.4 | 410.5 | 0 | 0 |
| 142 | 848.8 | 373.8 | 276.2 | 193.5 | 0 |
| 143 | 728.5 | 276.1 | 92 | 216.4 | 0 |
| 144 | 696.2 | 293.7 | 0 | 275.2 | 0 |
| 145 | 702.6 | 145.3 | 667.8 | 0 | 0 |
| 146 | 721.1 | 137.2 | 338.4 | 220.9 | 0 |
| 147 | 806.4 | 155.1 | 172 | 406.9 | 0 |
| 148 | 675.5 | 131.8 | 0 | 459.6 | 0 |
| 149 | 1265 | 0 | 1141.1 | 0 | 0 |
| 150 | 863.5 | 0 | 587.5 | 370.7 | 0 |
| 151 | 621.4 | 0 | 149.8 | 352.7 | 0 |
| 152 | 863.9 | 0 | 0 | 735.9 | 0 |
| 153 | 579.1 | 239.9 | 83.9 | 196.9 | 0 |
| 154 | 774 | 307.8 | 102.3 | 153.8 | 39.8 |
| 155 | 570.9 | 226.9 | 77.4 | 68.6 | 51.2 |
| 156 | 655.4 | 285.8 | 96.9 | 0 | 98.5 |
| 157 | 748.3 | 321.8 | 0 | 341.3 | 0 |
| 158 | 618.6 | 277.9 | 0 | 181.2 | 37 |
| 159 | 784.4 | 330.1 | 0 | 105.9 | 90.7 |

-continued

| Bead # | Area Ref. | Area P1 | Area P2 | Area P3 | Area P4 |
|---|---|---|---|---|---|
| 160 | 720.4 | 327.1 | 0 | 0 | 119.9 |
| 161 | 961.5 | 182.1 | 212.4 | 539.7 | 0 |
| 162 | 832.8 | 156.8 | 188.5 | 274.6 | 76.5 |
| 163 | 926.9 | 182.9 | 219.6 | 147.1 | 139.9 |
| 164 | 631.4 | 113.9 | 133.8 | 0 | 122.4 |
| 165 | 879 | 167.2 | 0 | 647 | 0 |
| 166 | 734.6 | 137.2 | 0 | 294.9 | 99.8 |
| 167 | 789.1 | 144.8 | 0 | 146.5 | 173.1 |
| 168 | 590.2 | 110.8 | 0 | 0 | 113.4 |
| 169 | 607.7 | 0 | 228.1 | 360.2 | 0 |
| 170 | 813.3 | 0 | 287.8 | 253.3 | 64.1 |
| 171 | 767.1 | 0 | 229.8 | 134.3 | 161.6 |
| 172 | 972.3 | 0 | 240 | 0 | 218.3 |
| 173 | 790.1 | 0 | 0 | 540.6 | 0 |
| 174 | 801.3 | 0 | 0 | 322.7 | 174.6 |
| 175 | 956.8 | 0 | 0 | 187.3 | 254.1 |
| 176 | 897.1 | 0 | 0 | 0 | 271 |
| 177 | 685 | 663.8 | 0 | 0 | 0 |
| 178 | 638.4 | 565.7 | 0 | 0 | 0 |
| 179 | 1000.2 | 851.4 | 0 | 0 | 0 |
| 180 | 766 | 713.3 | 0 | 0 | 0 |
| 181 | 1066.6 | 0 | 914.6 | 0 | 0 |
| 182 | 969.9 | 0 | 700.5 | 0 | 0 |
| 183 | 1327.4 | 0 | 1162.3 | 0 | 0 |
| 184 | 892.8 | 0 | 874.2 | 0 | 0 |
| 185 | 1049 | 0 | 27.5 | 893 | 0 |
| 186 | 694.6 | 0 | 0 | 546.3 | 0 |
| 187 | 743.9 | 0 | 26 | 495.7 | 0 |
| 188 | 659.9 | 0 | 0 | 452.3 | 0 |
| 189 | 842.1 | 0 | 0 | 0 | 258.6 |
| 190 | 697.5 | 0 | 0 | 0 | 163.9 |
| 191 | 830 | 0 | 0 | 0 | 237 |
| 192 | 647.7 | 0 | 0 | 0 | 171.1 |

These equations were analyzed to give ionization coefficients relative to the reference block for the four principle products observed in the mix and split synthesis.
The ionization coefficients are as follows:
Product P1 1.54, SD of 0.10
Product P2 1.38, SD of 0.06
Product P3 1.26, SD of 0.06
Product P4 0.51, SD of 0.03

The above results were then validated by comparing the data from the mass spectrometer with an independent method of amino acid analysis for a selected synthesis. The correlation validating this procedure for the four products is shown in the four graphs of FIGS. 5A, 5B, 5C and 5D.

Figure 6:
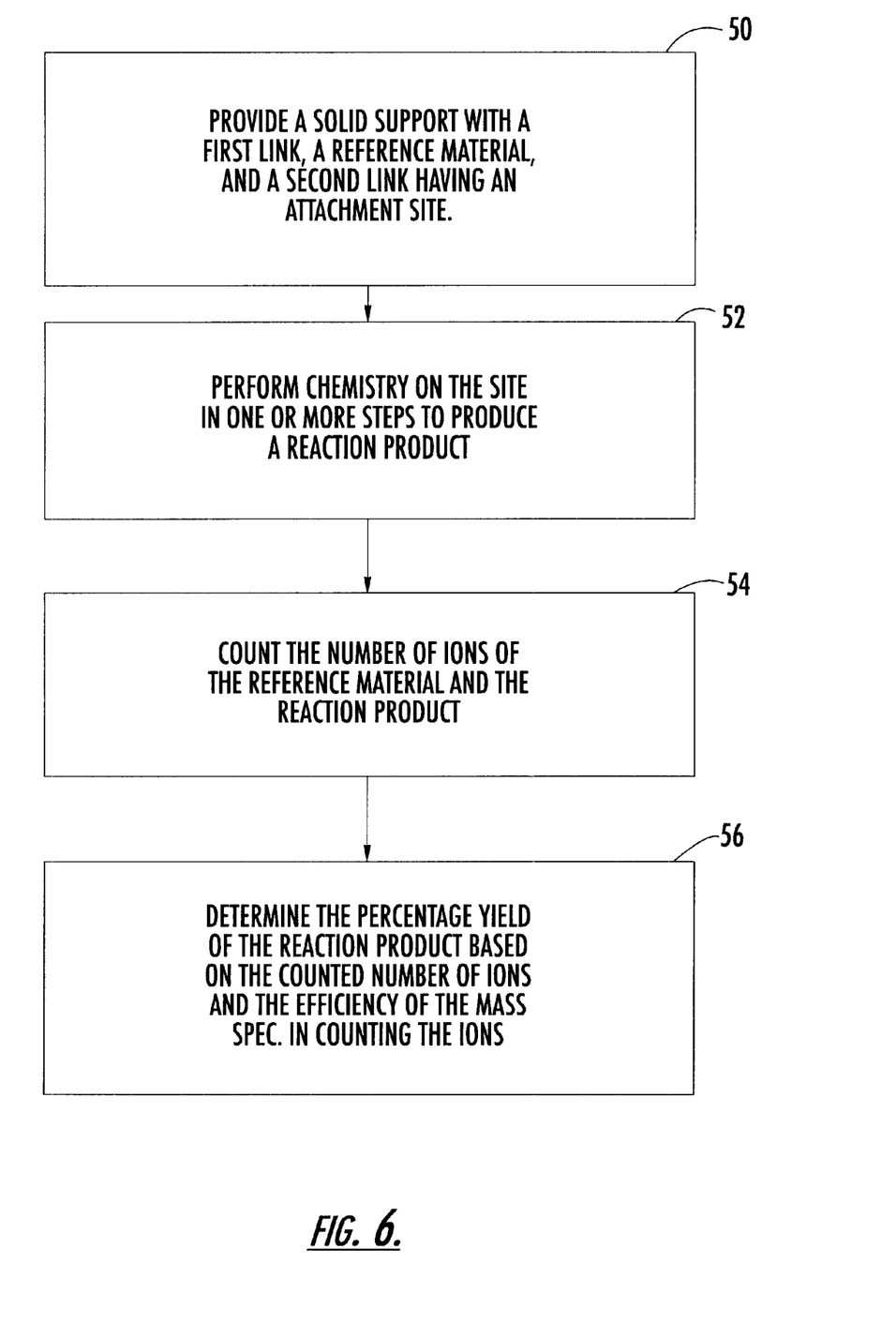
FIG. 6 is a flow chart illustrating one method for calculating the yield of reaction products when using a mass spectrometer according to the invention.

Referring now to FIG. 6, one method for calculating the yield of a reaction product will be described. As shown in step 50, a solid support is provided with a first link, a reference material, and a second link having an attachment site. Chemistry is performed on the attachment site in one or more steps to produce one or more reaction products as shown in step 52. The products and reference material are cleaved from the solid supports and analyzed in a mass spectrometer which counts the number of ions as shown in step 54. After compensating for the effects of the mass spectrometer, the yield of the reaction products is calculated by dividing the number of ions of the products by the number of ions of the reference material.

As previously described, the constructs of the invention may optionally include a ligand code to identify a ligand when the ligand is produced using mix and split techniques. The constructs of the invention may also optionally include a reaction condition code that is similar to the ligand code and may be used to identify various reaction conditions utilized when producing the ligand.

The use of such a reaction condition code is particularly useful when mix and split techniques are employed to allow the various reaction conditions to be identified once synthesis is complete. Types of reaction conditions that may be employed when producing the ligand include time, temperature, pressure, solvents, reagents, catalysts, and the like, as well as those described in Lutd-Friadjan Tietze, Reaction and Synthesis in the Organic Chemistry Library, University Science Books (1989) and Richard C. Larock, Comprehensive Organic Transformation —A Guide to Functional Group Preparation, VCH Publishers, Inc., (1989), the disclosures of which are hereby incorporated by reference.

The reaction conditions are encoded by assigning a code value to each condition and then linking the code to the solid support in a manner similar to that employed when linking the ligand codes as described generally in H. Mario Geysen, et al., "Isotope or Mass Encoding of Combinatorial Libraries, " Chem. & Biol. Vol. III, No. 8, pp. 679–688, August 1996 and PCT International No. PCT/US97/05701, previously incorporated by reference. However, it will be appreciated that other types of coding techniques may be employed, including Michael H. J. Ohlmeyer, et al., "Complex Synthetic Chemical Libraries Indexed with Molecular Tags", Proc. Natl. Acad. Sci. USA, Vol. 90, pp. 10922–10926, December 1993, A. W. Czarnik, "Encoding Strategies and Combinatorial Chemistry, Proc. Natl. Acad. Sci. USA Vol. 94, pp. 12738–12739, November 1997, U.S. Pat. No. 5, 770, 358, and the like. The disclosures of these references are herein incorporated by reference.

The use of such reaction condition codes is advantageous in that they allow a given reaction sequence to be optimized by exploring different reaction conditions. One non-limiting example of such a process is set forth in FIGS. 7–10. The process illustrated in FIGS. 7–10 is a synthesizing process which reacts monomers at discrete locations, and then mixes the solid supports and splits them into an array where another monomer is added. Such a process is similar to that described in PCT International Application No. PCT/US97/05701 and U.S. patent application Ser. No. 09/289, 211, filed Apr. 9, 1999, previously incorporated by reference. However, it will be appreciated that the reaction condition coding techniques of the invention may be used with other types of mix and split methods as are known in the art.

Figure 7:
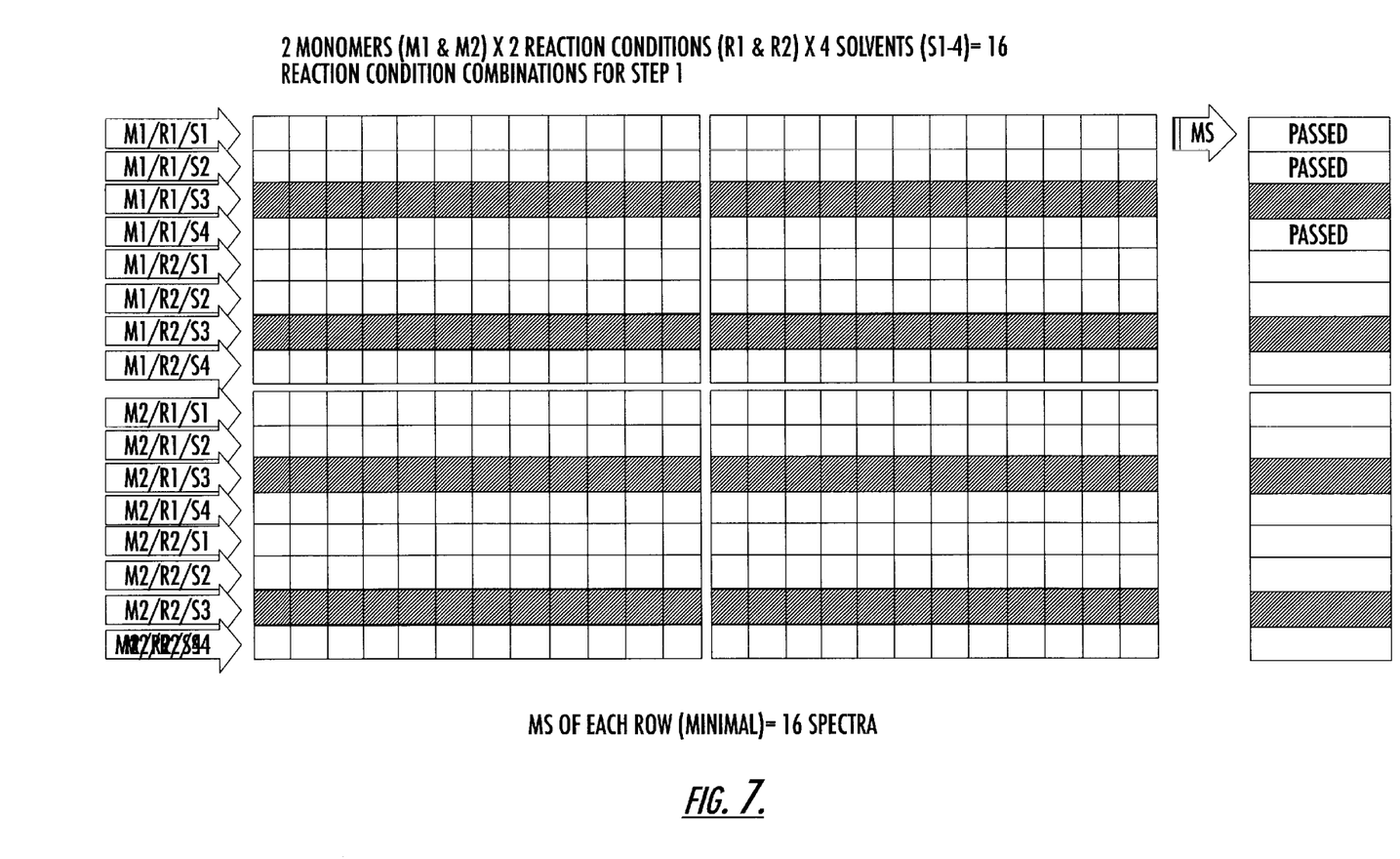
FIGS. 7–10 illustrate an exemplary method for optimizing chemical reactions according to the invention.

In FIG. 7, two monomers M1 and M2 are each subjected to two reaction conditions R1 and R2, using four solvents S1–S4. As shown in the right hand column, following this reaction screen step, an output is provided by the mass spectrometer which indicates whether the outcome is acceptable. For example, a percentage yield threshold value may be provided. If the calculated yield is above this value, the outcome is considered to be acceptable. In FIG. 7, the empty boxes indicate an acceptable condition while the darkened boxes indicate an unacceptable condition.

Figure 8:
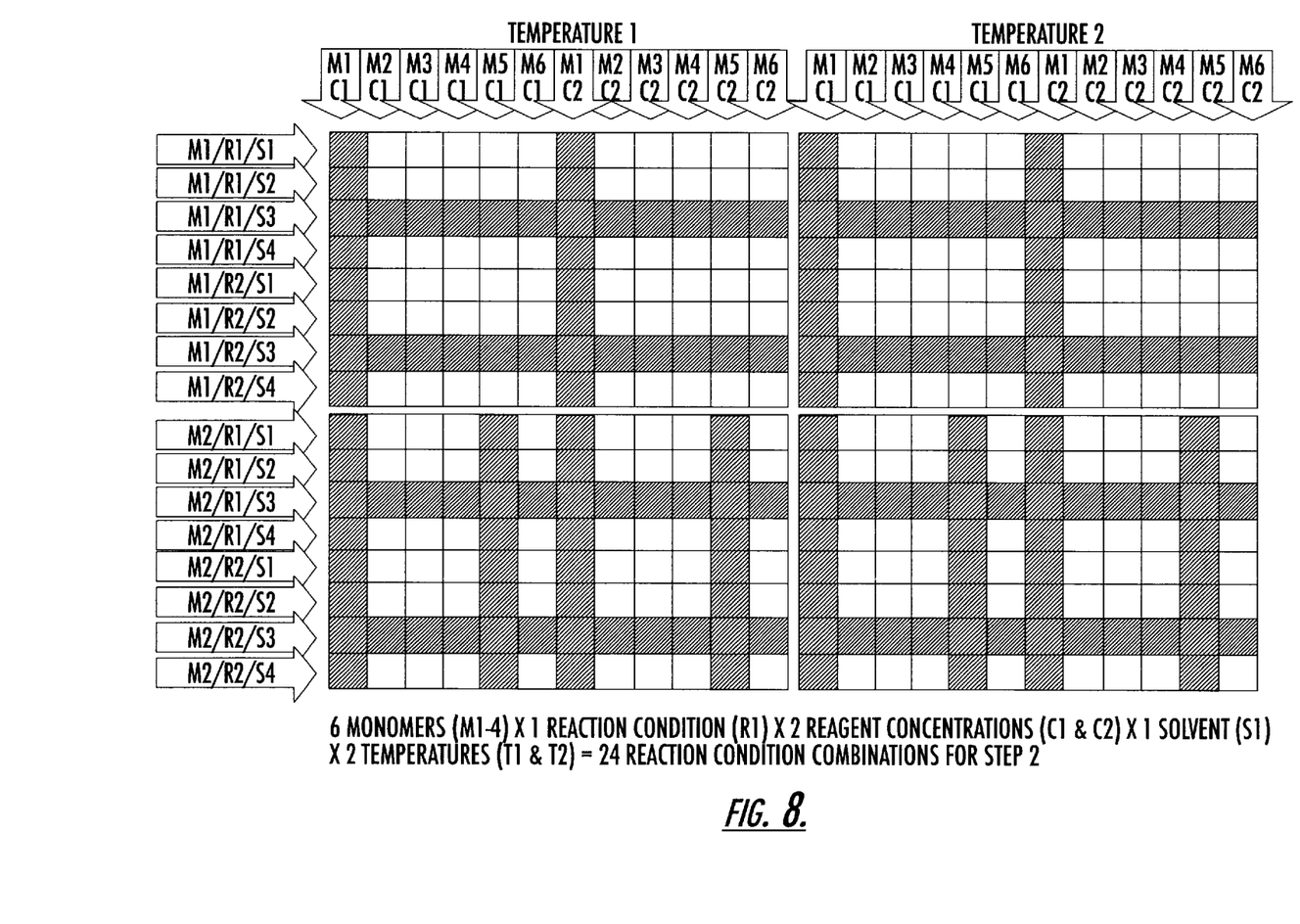
Figure 9:
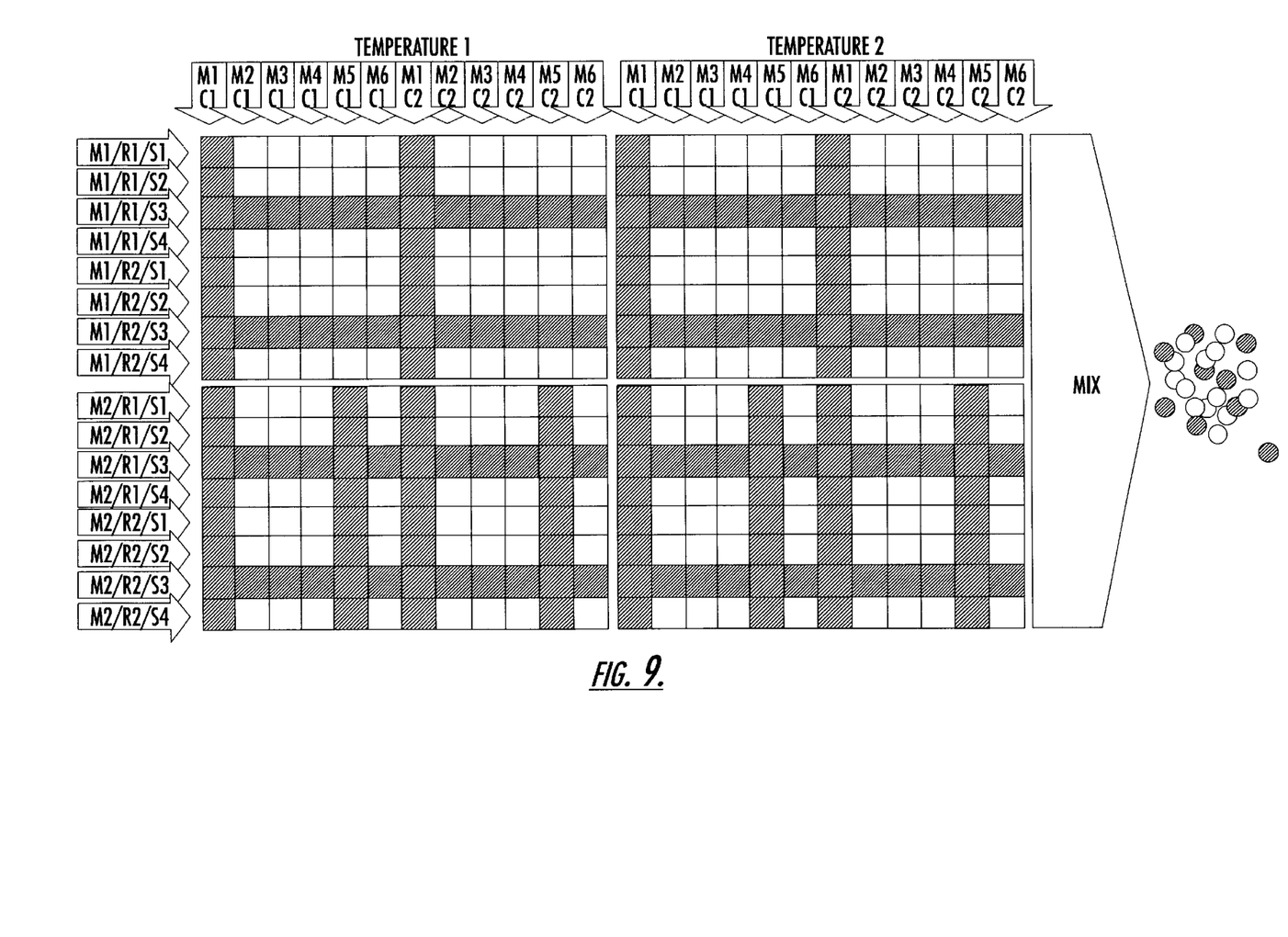

In FIG. 8, the process proceeds to step two, where each of the constructs is reacted with monomers M1–4 at one reaction condition R1, with two reagent concentrations C1 and C2, using one solvent S1, and at two temperatures T1 and T2. This produces 24 reaction condition combinations for step two. Samples are then taken from each well and evaluated under mass spectrometry to determine whether the outcome is acceptable or unacceptable. As shown in FIG. 9, the constructs are then pooled together, mixed and redistributed into an array of wells as illustrated in FIG. 10.

Figure 10:
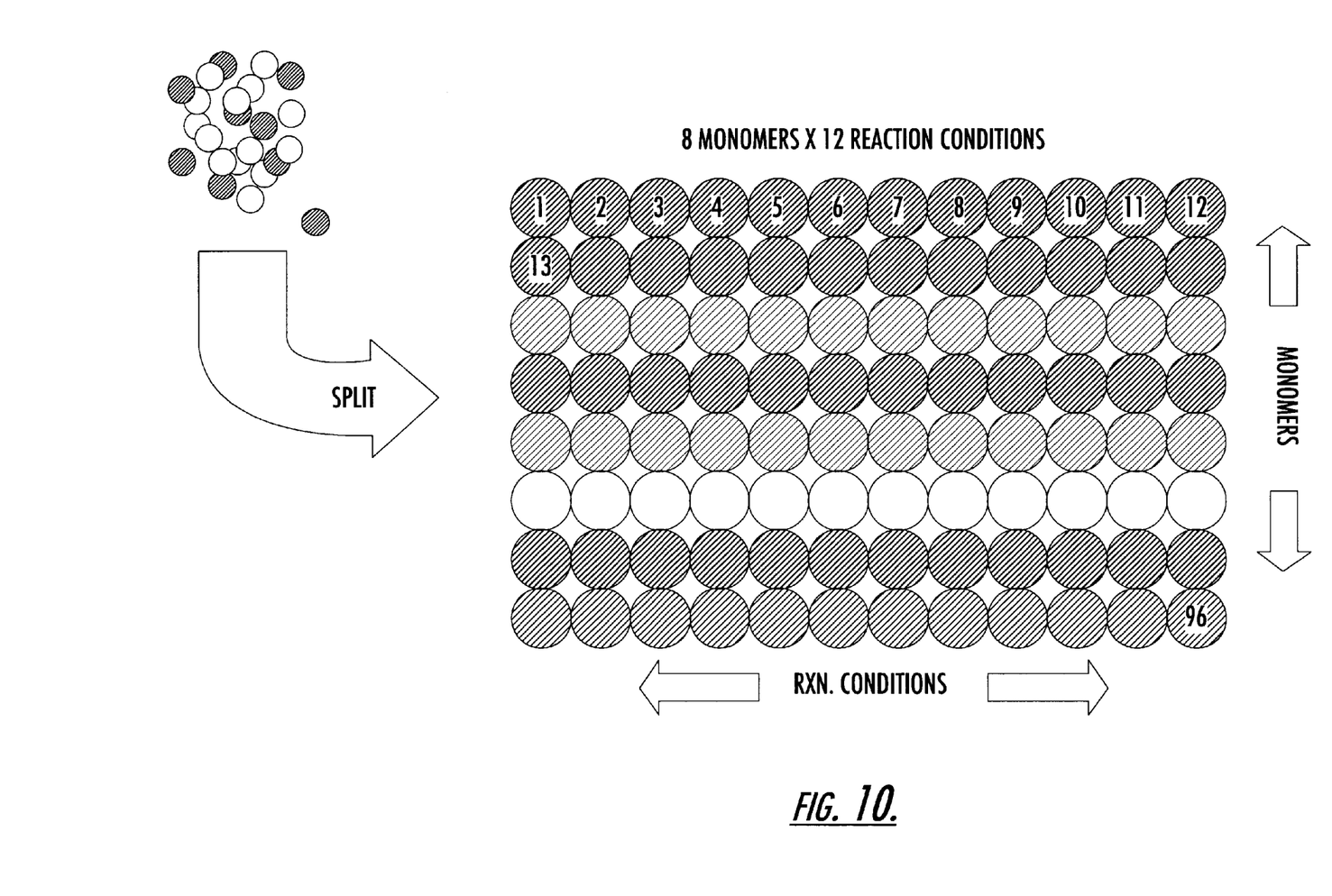

In the final step of FIG. 10, each of the constructs is reacted with eight monomers at 12 reaction conditions. These monomers and reaction conditions need not be encoded onto the construct because this information can be obtained from the discrete locations of each of the solid supports. After the last set of reactions, the solid supports may be evaluated using mass spectrometry to determine final yield results. Because the solid supports were mixed and split, those producing an acceptable yield may be decoded to determine the particular monomers as well as the reaction conditions employed when producing the ligand. Hence, a chemist is able to identify the most favorable reaction conditions merely by decoding the reaction condition code of the construct.

The invention has now been described in detail for purposes of clarity and understanding. However, it will be appreciated that certain changes and modifications may be practiced within the scope of the appended claims.

What is claimed is:

1. A method for calculating the yield of a reaction product, the method comprising:
   providing a solid support with a first link, a reference material, and a second link having an attachment site;
   performing chemistry on the attachment site of the second link in one or more steps to produce a reaction product;
   measuring the amount of the reference material and the reaction product;
   determining the percentage yield of the reaction product based at least in part on the amount of measured reference material and the amount of measured reaction product.

2. A method as in claim 1, wherein the chemistry performing step comprises reacting the attachment site with a chemical building block to produce the reaction product.

3. A method as in claim 1, wherein the chemistry performing steps comprise reacting the attachment site with a first chemical building block to produce an intermediate product, and reacting the intermediate product with a second chemical building block to produce the reaction product.

4. A method as in claim 1, wherein the chemistry performing steps comprise reacting the attachment site with a first chemical building block to produce an intermediate product, and carrying out a chemical transformation of the intermediate reaction product to produce the reaction product.

5. A method as in claim 1, wherein the measuring step comprises counting the number of ions of the reference material and the reaction product.

6. A method as in claim 5, wherein the determining step comprises dividing the number of counted ions of the reaction product by the number of counted ions of the reference material.

7. A method for calculating the yields of the products of a reaction using a mass spectrometer, the method comprising:
   counting the number of ions of reference materials and reaction products that have been cleaved from multiple solid supports;
   determining the efficiency with which the reference materials and the products may be detected by a given mass spectrometer, wherein the efficiency relates at least in part to the efficiency with which the reference materials and the products are transferred from droplet phase to gas phase or are transferred to a low pressure side of the mass spectrometer; and
   determining the percentage yield of each reaction product based at least in part on the amount of the number of counted ions of the associated reference material, the counted number of ions for the reaction product, and the determined efficiency.

8. A method as in claim 7, wherein the efficiency determining step comprises producing multiple equations where each equation sets the ion counts of each reference material equal to the sum of a coefficient multiplied by the ion counts of the associated reaction product, solving for the coefficients of the equations, and wherein the yield determining step comprises multiplying the coefficients by the number of ion counts of each product and dividing the product by the number of ion counts of the associated reference material.

9. A method for evaluating the yields of multiple chemical reactions, the method comprising:
   providing multiple solid supports which each include with a first link, a reference material, and a second link having an attachment site;
   performing chemistry on the attachment sites of the second links in one or more steps and under different reaction conditions to produce a reaction product for each solid support; and
   determining the percentage yield of the reaction products based at least in part the amount of measured reference material; and
   associating the yields with the reaction conditions.

10. A method as in claim 9, wherein the solid supports further include a reaction condition code indicative of the reaction conditions used when performing the chemistries, and further comprising decoding the reaction condition codes to determine the reaction conditions.

11. A method as in claim 10, further comprising mixing and splitting the solid supports when performing the chemistry steps.

12. A method as in claim 9, further comprising counting the number of ions of the reference material and the product from each of the solid supports, determining the efficiency with which the reference materials and the products may be detected by a mass spectrometer, and determining the percentage yield of each reaction product based at least in part on the ion counts for each reference material, the ion counts for each reaction product, and the determined efficiencies.

13. A method as in claim 12, wherein the efficiency determining step comprises producing multiple equations where each equation sets the ion counts of each reference material equal to the sum of a coefficient multiplied by the ion counts of the associated reaction product, solving for the coefficients of the equations, and wherein the yield determining step comprises multiplying the coefficients by the number of ion counts of each product and dividing the product by the number of ion counts of the associated reference material.

14. A method for calculating the yield of a reaction product, the method comprising:
   providing a construct with a first link, a reference material, and a second link having an attachment site;
   performing chemistry on the attachment site of the second link in one or more steps to produce a reaction product;
   measuring the amount of the reference material and the reaction product;
   determining the percentage yield of the reaction product based at least in part on the amount of measured reference material and the amount of measured reaction product.

15. A method as in claim 14, wherein the construct comprises a solid support.

* * * * *